(12) United States Patent
Turnell et al.

(10) Patent No.: US 10,304,562 B2
(45) Date of Patent: *May 28, 2019

(54) MEDICAL REMINDER AND DISPENSING DEVICE

(71) Applicants: Tracy Turnell, Port Coquitlam (CA); Abbas Beigi, Port Coquitlam (CA)

(72) Inventors: Tracy Turnell, Port Coquitlam (CA); Abbas Beigi, Port Coquitlam (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/899,912

(22) Filed: Feb. 20, 2018

(65) Prior Publication Data
US 2018/0174674 A1     Jun. 21, 2018

Related U.S. Application Data

(63) Continuation of application No. 13/199,575, filed on Sep. 1, 2011, now Pat. No. 9,934,365.

(60) Provisional application No. 61/402,680, filed on Sep. 1, 2010.

(51) Int. Cl.
| | |
|---|---|
| *G16H 20/13* | (2018.01) |
| *A61J 7/04* | (2006.01) |
| *G06F 19/00* | (2018.01) |

(52) U.S. Cl.
CPC ............ *G16H 20/13* (2018.01); *A61J 7/0418* (2015.05); *A61J 7/0427* (2015.05); *A61J 7/0481* (2013.01); *G06F 19/00* (2013.01); *G06F 19/3462* (2013.01)

(58) Field of Classification Search
CPC .... A61J 7/0481; A61J 7/0427; A61J 2205/70; A61J 7/0084; A61J 7/0418; A61J 7/049; A61J 2200/30; A61J 2205/50; A61J 2205/60; A61J 7/0436; G06F 19/00; G06F 19/3462; G06F 19/3418; G06F 19/326
USPC ............ 340/309.7, 309.4, 457, 534, 539.12, 340/539.13, 539.22, 573.1, 5.52, 7.51
See application file for complete search history.

(56) References Cited

U.S. PATENT DOCUMENTS

| | | | |
|---|---|---|---|
| 5,347,453 | A | 9/1994 | Maestre |
| 5,408,443 | A | 4/1995 | Weinberger |
| 5,582,323 | A | 12/1996 | Kurtenbach |
| 5,642,731 | A | 7/1997 | Kehr |
| 5,646,912 | A | 7/1997 | Cousin |
| 5,850,344 | A | 12/1998 | Conkright |

(Continued)

FOREIGN PATENT DOCUMENTS

| | | |
|---|---|---|
| CA | 2283391 A1 | 9/1998 |
| WO | 9838909 A1 | 9/1998 |

*Primary Examiner* — Daniel Previl
(74) *Attorney, Agent, or Firm* — The Webb Law Firm

(57) ABSTRACT

A medication reminder and dispensing device includes a housing having at least one opening and at least one drawer containing at least one dose of a medication to be delivered to a patient. The drawer is slidably positioned in the opening and configured to move from a closed position to an open position. The device also includes at least one electromagnet connected to the housing or drawer configured to be transitioned between a first state and a second state. When in the first state, the electromagnet is configured to maintain the drawer in the closed position. When in the second state, the drawer automatically moves to the open position. The device also includes a processor configured to cause the at least one electromagnet to transition from the first state to the second state based on the pre-programmed schedule, thereby causing the drawer to automatically move to the open position.

20 Claims, 18 Drawing Sheets

(56) References Cited

U.S. PATENT DOCUMENTS

| | | | |
|---|---|---|---|
| 5,927,540 A * | 7/1999 | Godlewski | G07F 17/0092 |
| | | | 221/103 |
| 5,954,641 A | 9/1999 | Kehr et al. | |
| 6,085,752 A | 7/2000 | Kehr et al. | |
| 6,102,855 A | 8/2000 | Kehr et al. | |
| 6,263,259 B1 | 7/2001 | Bartur | |
| 6,332,100 B1 | 12/2001 | Sahai et al. | |
| 6,471,087 B1 | 10/2002 | Shusterman | |
| 7,263,411 B2 | 8/2007 | Shows et al. | |
| 9,149,405 B2 | 10/2015 | Braun | |
| 9,934,365 B2 * | 4/2018 | Turnell | A61J 7/0418 |
| 2003/0216624 A1 * | 11/2003 | Lin | A61B 5/0002 |
| | | | 600/300 |
| 2009/0138122 A1 * | 5/2009 | Wagner | A61G 12/001 |
| | | | 700/226 |
| 2011/0234419 A1 | 9/2011 | Churbock et al. | |

* cited by examiner

| | A | B | C | D | E | F | G | H |
|---|---|---|---|---|---|---|---|---|
| DAY 1 | | | | | | | | |
| DAY 2 | | | | | | | | |
| DAY 3 | | | | | | | | |
| DAY 4 | | | | | | | | |
| DAY 5 | | | | | | | | |
| DAY 6 | | | | | | | | |
| DAY 7 | | | | | | | | |

PRESCRIPTION TEMPLATE REPORT

FIG. 5

|  | A | B | C | D | E | F | G | H |
|---|---|---|---|---|---|---|---|---|
| DAY 1 | 1 Nova-Betahistine<br>1 Vit D W/CA<br>1 Aspirin |  | 1 Nova-Betahistine | 1 Nova-Betahistine | 1 Lipitor<br>1 Accupril | 1 Nova<br>Betahistine<br>2 Vitalux<br>2 Nova<br>Venlafaxine |  |  |
| DAY 2 | 1 Nova-Betahistine<br>1 Vit D W/CA<br>1 Aspirin |  | 1 Nova-Betahistine | 1 Nova-Betahistine | 1 Lipitor<br>1 Accupril | 1 Nova<br>Betahistine<br>2 Vitalux<br>2 Nova<br>Venlafaxine |  |  |
| DAY 3 | 1 Nova-Betahistine<br>1 Vit D W/CA<br>1 Aspirin | 1 Fosamax | 1 Nova-Betahistine | 1 Nova-Betahistine | 1 Lipitor<br>1 Accupril | 1 Nova<br>Betahistine<br>2 Vitalux<br>2 Nova<br>Venlafaxine |  |  |
| DAY 4 | 1 Nova-Betahistine<br>1 Vit D W/CA<br>1 Aspirin |  | 1 Nova-Betahistine | 1 Nova-Betahistine | 1 Lipitor<br>1 Accupril | 1 Nova<br>Betahistine<br>2 Vitalux<br>2 Nova<br>Venlafaxine |  |  |
| DAY 5 | 1 Nova-Betahistine<br>1 Vit D W/CA<br>1 Aspirin |  | 1 Nova-Betahistine | 1 Nova-Betahistine | 1 Lipitor<br>1 Accupril | 1 Nova<br>Betahistine<br>2 Vitalux<br>2 Nova<br>Venlafaxine |  |  |
| DAY 6 | 1 Nova-Betahistine<br>1 Vit D W/CA<br>1 Aspirin |  | 1 Nova-Betahistine | 1 Nova-Betahistine | 1 Lipitor<br>1 Accupril | 1 Nova<br>Betahistine<br>2 Vitalux<br>2 Nova<br>Venlafaxine |  |  |
| DAY 7 | 1 Nova-Betahistine<br>1 Vit D W/CA<br>1 Aspirin |  |  | 1 Nova-Betahistine | 1 Lipitor<br>1 Accupril | 1 Nova<br>Betahistine<br>2 Vitalux<br>2 Nova<br>Venlafaxine |  |  |

FIG. 18

ND DISPENSING
MEDICAL REMINDER AND DISPENSING DEVICE

CROSS REFERENCE TO RELATED APPLICATIONS

This application is a continuation of U.S. patent application Ser. No. 13/199,575, filed Sep. 1, 2011, which claims priority to U.S. Provisional Patent Application No. 61/402,680, filed Sep. 1, 2010, the contents of each of which are incorporated by reference herein in their entireties.

BACKGROUND OF THE INVENTION

Field of the Invention

The present invention relates to the field of medication reminder and dispensing devices which allow patients to be visually or audibly reminded of medication dosages and timing of such administration.

Description of Related Art

A long recognized problem in the health care industry is patient non-compliance with the administration of medications. If prescribed medication is not taken at the correct time, or in the correct dosage, or is not taken at all, the medication will not have the intended effects which can be dangerous or even fatal. Monitoring and control is often essential for such compliance. This problem is exacerbated in the elderly and in mentally ill patients. Many elderly patients arrive in emergency departments, often quite ill, for the very simple reason of non-compliance with medication regimes. They cannot remember to take their medications at the correct time and dose. Likewise, nearly half of patients entering nursing homes do so for the reason that they cannot cope with medication dosage compliance. The situation is not helped by the fact that, as a person ages, there is a concomitant increase in the number of medical problems he/she must address and precisely at a time in life when remembering becomes more challenging.

Often, the government or family members will pay for private home care workers to attend at the home of the elderly or mentally ill patients to ensure medication administration compliance. The cost of these visits (often several times in one day) is an enormous financial burden, whether borne by family or government. It is clear that there are both health and economic benefits to a reliable medical reminder and dispensing system.

There are a variety of automatic pill dispensers purportedly aimed at some aspects of the pill dispensing problem in the related art. Some provide dispensing of pills at pre-determined time intervals and some provide feedback to call centres and visual or audible alarm messages. All have shortcomings in one or more of the following areas: complexity, cost, flexibility, ease of use, and error resistance.

U.S. Pat. No. 6,332,100 (granted to Interactive Medical Developments LC on Dec. 18, 2001) discloses a medical reminder and medication dispenser device which provides a series of cylindrical tubes, each holding pre-loaded dispenser cups 100 containing particular medications to be taken at allotted times. These canisters or dispensing cups are pre-loaded by a caregiver. There are LCD (32) screen and audio alarm features along with a communication feature with a call centre. The mechanism of dispensing the canisters is prone to error and a limiting feature of this device.

U.S. Pat. No. 5,582,323 (granted to United Home Technologies on Dec. 10, 1996) describes a dispenser apparatus not completely dissimilar that in later filed the U.S. Pat. No. 6,332,100 patent above, but it has no means to protect for patient overdosing nor does it provide emergency communication to local caregivers as opposed to call centre.

U.S. Pat. No. 5,646,912 (granted to Damon Cousin on Jul. 8, 1997) describes another dispensing and monitoring device with clear similarities to 6,332,100 (there are controls against overdosing) but such controls are complex (difficult for patient usage and compliance) and the dispensing compartments are used over and over hence there is the issue of contamination and reside build-up.

Canadian Patent Application 2,283,391 (filed originally as international application WO98/38909 by Informedix, Inc.) describes another dispensing device but clearly not designed for patients with compromised mental functions i.e. the patients must have the ability to read and discern dosages of drug to be taken from each compartment (see page 31—in which is it shown that the compartments in the tray are designed to hold not just a particular "dose" but a week or more supply of given drug). There is a high risk of overdosing and non-compliance.

Informedix Inc. has a series US Patents in place covering drug dispensing devices including U.S. Pat. No. 6,102,855 from which WO98/38909 claims priority, U.S. Pat. Nos. 6,085,752, 5,954,641, and 5,642,731. This family of patents all appears to have the same drawback as Canadian 2,283,391, namely poor protection against overdosing or incorrect dosing. It appears largely up to the patient to be cognizant enough to read and follow the dosage instructions provided by the device.

U.S. Pat. No. 5,347,453 (was granted to Maestre on Sep. 13, 1994) covers a medication holder device (with alarm) which also requires patient selection and compliance with dosing regimen.

U.S. Pat. No. 6,263,259 (was granted to Bartur on Jul. 17, 2001) describes another reminder device in which pills are removed, in accordance with a programmed dosage regime, from a pez-like dispenser. A single pill or tablet is dispensed by each revolution of the delivery drum 120 by way of the actuator 124. The patient appears to need to follow the specific dosage instructions provided by the device in order not to overdose.

U.S. Pat. No. 5,850,344 (was granted to Profile Systems LLC on Dec. 15, 1998) is focused on the monitoring and feedback aspects of a device while the dispensing portion 25 is considered optional. In fact, there is no teaching as to exactly how the dispensing portion works or how it prevents overdosing. In other words, there are no mechanics provided in relation to dispensing portion 25 and how it would achieve the desired goals.

It is an object of the present invention to obviate or mitigate the above disadvantages.

SUMMARY OF THE INVENTION

The present invention provides a medication reminder and dispensing system which comprises a reminder/dispenser device comprising i) a housing with a plurality of medication holding drawers situated therein, ii) a means to enable slidable movement of each drawer to an open position relative to the housing, to expose the interior of the drawer, which means conversely allows secure closure of each drawer relative to the housing, iii) means to prevent complete detachment of each drawer from the housing, iv) a programmable communication means for entering, storing, retrieving and signaling messages to a patient, said messages prompting patient to take medications in one or more drawers; v) actuating means to have the device identify the specific one or more drawers, at a selected time, which must be opened and emptied of their medication contents according to pre-programmed dosing schedule and a means to visually, aurally or audibly identify the drawer to the patient and vi) feedback means to allow patient to confirm to device that drawer emptied in accordance with pre-programmed dosing schedule, said system further including a communication line interface operatively coupled to device for communication to remote monitoring station, said interface being capable of receiving and communicating signals from device, including a signal that patient in non-compliance with drawer emptying and feedback means.

This system provides an elegantly simple device, absent unnecessary moving parts which are prone to breakage and device failure. Medication dosages are programmed into the system but can be easily and remotely adjusted. The patient 1) is notified (by visual and/or aural means) when medication is due to be taken and 2) is directed to the particular drawer from which medication is to be removed. There is no guess work expected of the patient in waiting for medication to drop from within a unit onto a central tray or to be released by dispenser cups through chutes, potentially getting stuck or tipped or otherwise compromised. The patient does not have to count pills to be taken or engage with the device other than to notice the visual or aural message, remove medication from an open drawer and close the drawer.

There is no risk of overdosing of a properly pre-loaded device in accordance with this invention as each drawer, once opened, represents the medication regime required to be taken at that point in time. If there is non-compliance with the drawer emptying by the patient, the system provides a feedback mechanism to one or more of a) the patient him or herself; b) a remote call centre; and c) family members or other patient contacts. At this point, there is no guess work on the part of the caregiver as to what dosage was missed, which is a clear limitation of some prior devices. Within the scope of the present invention, there is a direct and irrefutable drawer match to show a missed dose and at what time the dose was missed.

More specifically, within this system, the device is programmed with medication dosing schedule for a patient such that any individual (caregiver, family member or the like) can, with confidence, fill each of the drawers with the pre-determined medication (pills, tablets, chews or even liquids, as will be explained further below). The device can then be left with the patient and will provide messages to the patient indicating which drawers have to be emptied and "taken" at selected, pre-programmed intervals. As will be described further below, there are built in feedback mechanisms to ensure monitoring and compliance with the pre-programmed dosage regimes.

The multiple drawer grid arrangement is a form deliberately chosen. Any number of drawers can be used in devices of varying sizes. Likewise the drawers can be made of varying sizes to accommodate specific usages and patient requirements. For-example transplant recipients often take a program of multiple pills which regime may necessitate a larger drawer system. As well as being flexible to patient needs, the symmetrical grid arrangement allows ease of loading and significantly reduces margins of loading error.

These and other objects and advantages of the present invention will become more apparent to those skilled in the art upon reviewing the description of the preferred embodiments of the invention, in conjunction with the figures and examples.

BRIEF DESCRIPTION OF THE DRAWINGS

The following figures set forth embodiments in which like reference numerals denote like parts. Embodiments are illustrated by way of example and not by way of limitation in all of the accompanying figures.

FIG. 5 is a depiction of a prescription template which is representation of a complementary drawer grid arrangement of one device in accordance with the present invention, showing 56 drawers;

FIG. 18 is a schematic drawing of a reminder report which can be filled out by a caregiver loading medications into a medical reminder and dispensing device according to an aspect of the present invention.

PREFERRED EMBODIMENTS OF THE INVENTION

Figure 1:
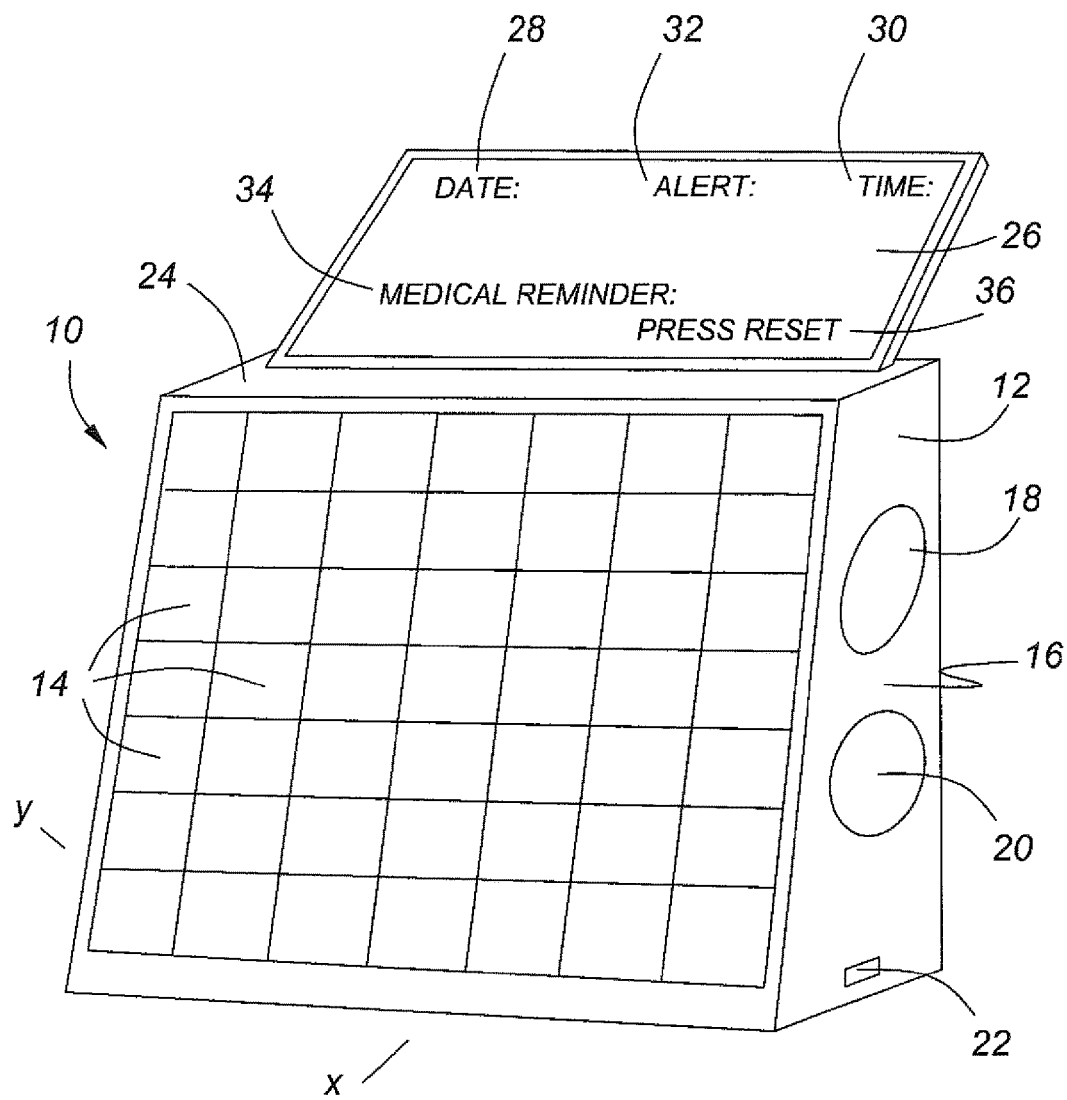
FIG. 1 is perspective view of a device in accordance with one aspect of the present invention.

The following detailed description illustrates the invention by way of example and not by way of limitation. The description will clearly enable one skilled in the art to make and use the invention, and describes several embodiments, adaptations, variations and alternatives and uses of the invention, including what we presently believe is the best mode for carrying out the invention. It is to be clearly understood that routine variations and adaptations can be made to the invention as described, and such variations and adaptations squarely fall within the spirit and scope of the invention.

In other words, the invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured. Similar reference characters denote similar elements throughout various views depicted in the figures.

This description of preferred embodiments is to be read in connection with the accompanying drawings, which are part of the entire written description of this invention. In the description, corresponding reference numbers are used throughout to identify the same or functionally similar elements. Relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and are not intended to require a particular orientation unless specifically stated as such. Terms including "inwardly" versus "outwardly," "longitudinal" versus "lateral", "adjacent" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. Interconnected, as used herein, generally refers to the relationship between the platforms and adjacent blocks. The term "operatively connected" is such an attachment, coupling or connection that allows the pertinent structures to operate as intended by virtue of that relationship.

In the present disclosure and claims (if any), the word "comprising" and its derivatives including "comprises" and "comprise" include each of the stated integers but does not exclude the inclusion of one or more further integers.

One embodiment of the present invention is shown in FIGS. 1 to 4, wherein like numerals used throughout the Figures and description represent like elements. As depicted in FIG. 1, there is provided a reminder/dispenser device generally indicated at 10, which includes housing 12 within which is situated a plurality of medication holding drawers 14, all shown in the fully closed position. Along one side wall 16 of housing 12, there is provided a reset button 18, speaker 20 and USB port 22. Along top surface 24 of housing 12 is position LCD screen 26 which presents visual messages to the patient in regards to a multitude of information including, but not limited to:
1) Date (28);
2) Time (30);
3) Alerts (32) regarding name of current medication taken at selected current time and exact amount of medication which will be available in the open drawer;
4) Special instructions (34) in regards to requirements of the medication, for example, "take with food" or "no dairy" or "take with 8 oz. water"; and
5) Instruction to PRESS RESET (36).

Figure 2:
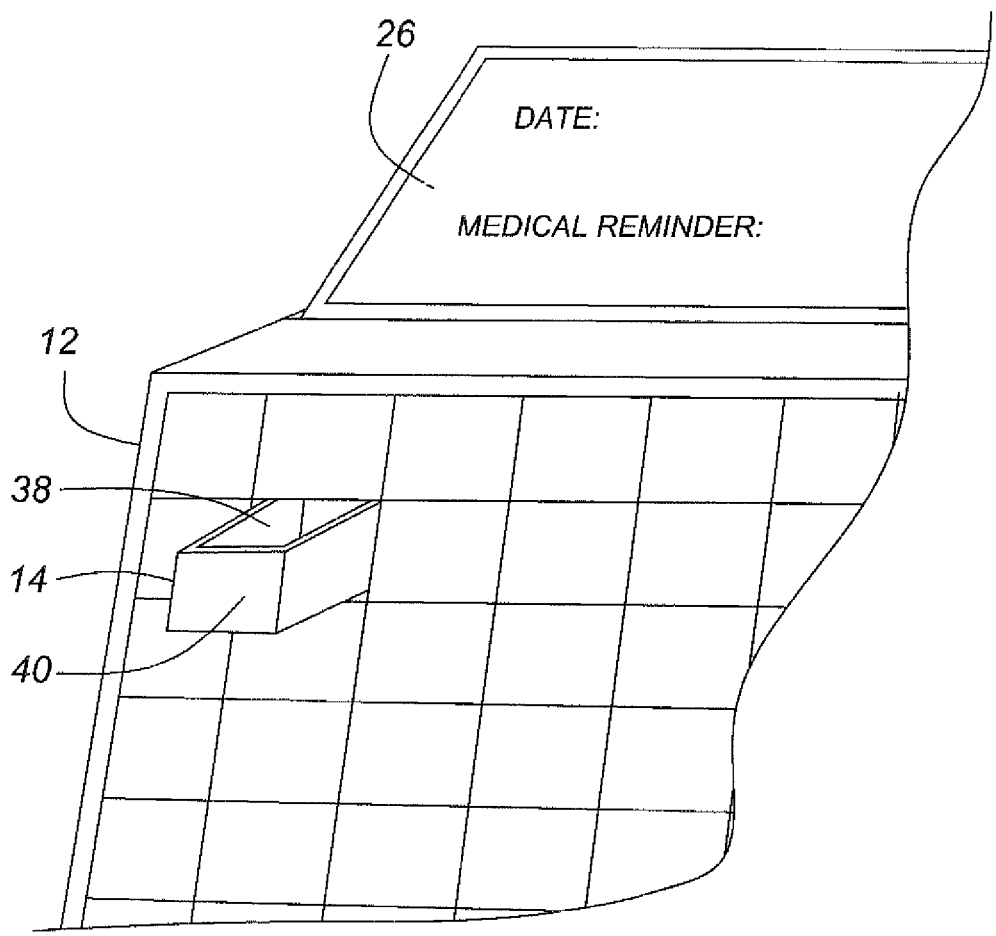
FIG. 2 is a perspective view of the device of FIG. 1 showing a drawer in an open position.

FIG. 2 depicts housing 12 with drawer 14 in an open position thereby exposing interior 38. In one embodiment, a fibre optic light (shown as yellow hue) is provided in the base of the drawer, thus giving light to interior 38 when drawer is in open configuration. This way, the patient is further alerted as to the "correct" drawer from which to remove medication at any given, selected time, in accordance with pre-programmed dosing schedule. In an alternative embodiment, the lighting may be configured only within front face 40 of the drawer. In yet another embodiment, lighting may be provided in both interior 38 and front face 40. The purpose of the lighting is to alert the patient and identify the drawer to be emptied at any given time. Lighting is an easy and simple way to achieve this although it is to be understood that other means would work and are contemplated within the scope of this invention. For example, the drawers could each be numbered or lettered and screen 26 could simply direct the patient as to which numbered or lettered drawer to open or to empty (should drawer opening occur automatically, a preferred feature).

Figure 3:
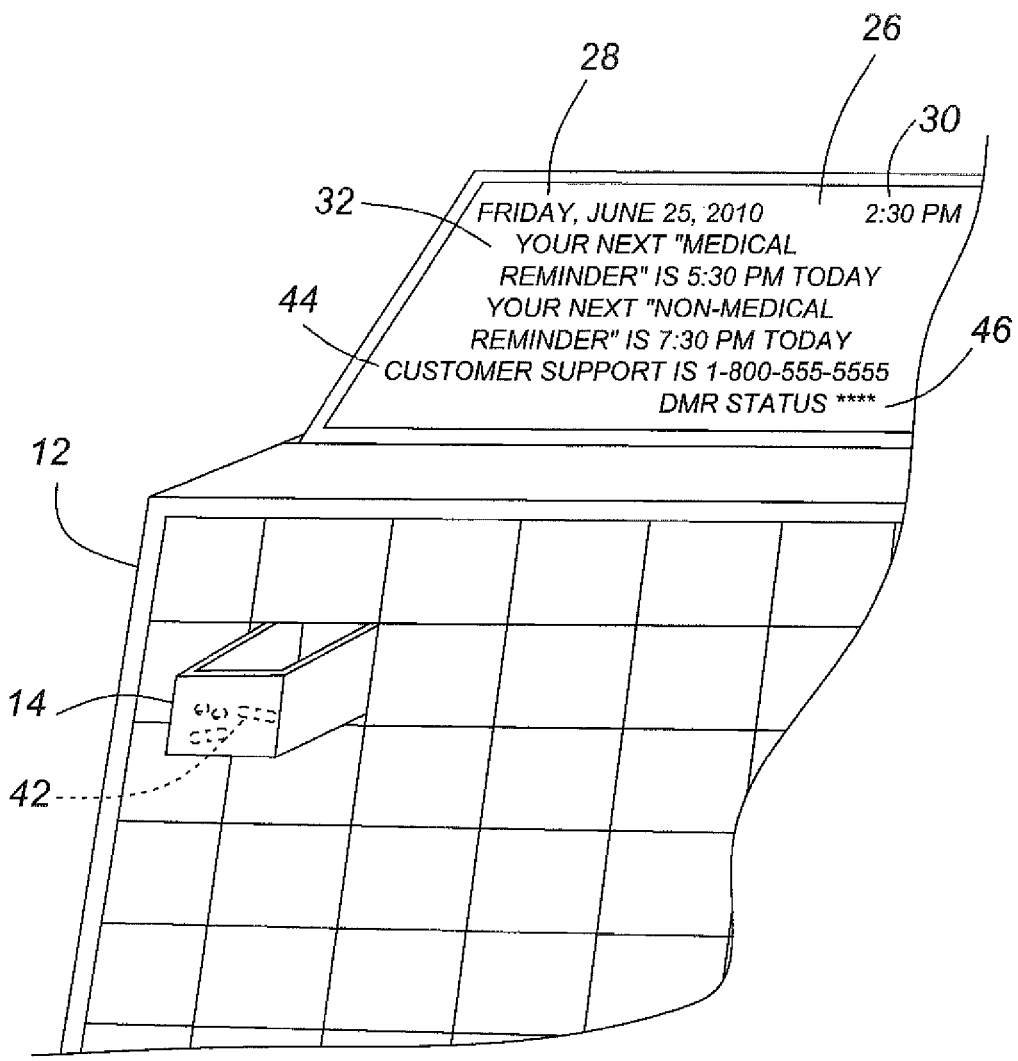
FIG. 3 is a perspective view of a device in accordance with one aspect of the present invention showing a drawer, containing medication, in an open position.

This inventive concept is further exemplified in FIG. 3, which depicts housing 12, and drawer 14 in an open position and containing medications 42, such medications being exposed to and viewable by the patient. In a similar fashion to FIG. 1, FIG. 3 provides screen 26 showing date 28, time 30, alerts 32 and in addition, shows a customer support line 44 and operational status update 46.

Figure 4:
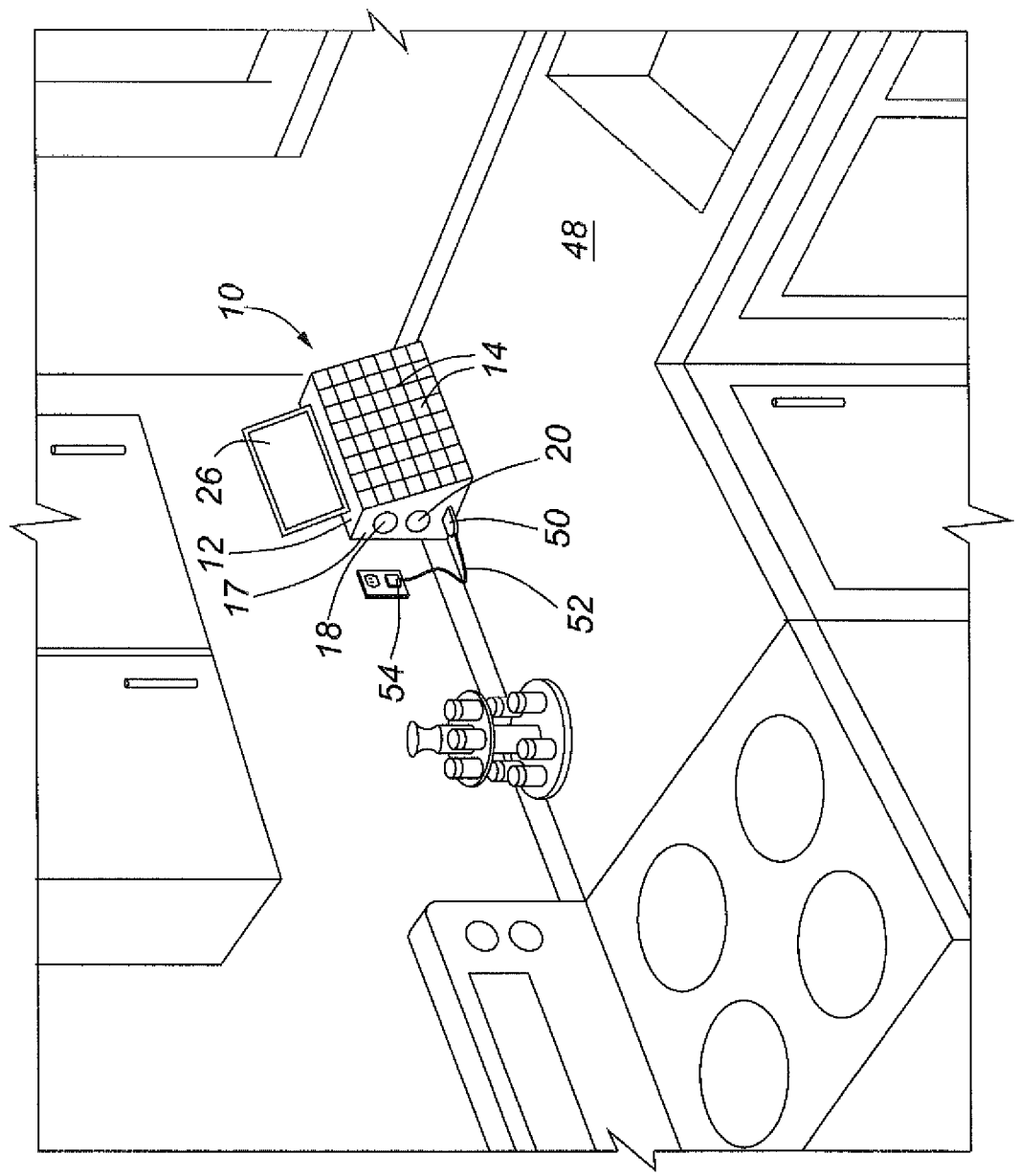
FIG. 4 is a perspective view of a device in accordance with one aspect of the present invention shown in situ on a kitchen counter of a patient's home.

FIG. 4 shows one possible location of use of reminder/dispensing device 10 in situ at the home of a patient. It is preferred that device 10 be centrally and conveniently located within the home of the patient, in this case, on kitchen counter 48. Depending on the particular patient, other locations may be equally suitable. In contrast to FIG. 1, speaker 20 and reset button 20 are depicted on side 17 of housing 12 as opposed to side 16. Power is supplied to device 10 by way of the connection of electrical portal 50 on housing 12 to wall switch 54 via cord 52. Preferably, power is 110 AC. In an alternative and equally useful embodiment, device 10 may be battery powered thereby obviating the requirement of an electrical connection. In another preferred embodiment, power may be supplied by a combination of battery and electrical power. It is contemplated that device 10 may be suitably powered via alternative energy means such as solar, by including as part of the system photovoltaic/solar panels and energy storage means.

It is preferred that the internal portion of the housing is cooled by an oscillating fan and venting screens.

FIG. 5 is a prescription template which is a representation of a complementary drawer grid arrangement of one device in accordance with the present invention, showing 56 drawers. As such, FIG. 5 is complementary to the device shown in any of FIGS. 1-4. It is to be understood that, while 56 is a preferred number of drawers, device 10 can be adapted and manufactured to accommodate more or fewer drawers, as required. For example, in another preferred embodiment, the device comprises 98 drawers (7 rows vertically by 14 rows horizontally).

In FIG. 1, an x axis and a y axis is shown for the purpose of illustrating how the drawers match the Prescription Template Report ("PTR") of FIG. 5, with the same x and y axes. The PTR is generated by input from caregiver, medical professional or other individuals and includes medication requirements, time for administration, quantity of medication, quantity of non-prescription medications and, for example, vitamins minerals or supplements as well as other variables. The PTR is then used to fill the drawers prior to use by the patient. Should a change in medication or instructions occur at any time, a new PTR will be generated. It is preferred that the PTR be generated by a remote server or customer support. A filled in PTR is provided as part of Example 4 and shown in FIG. 18.

In a preferred form of the invention, axis y represents a 7 day (one week) cycle of medications and as such there are seven rows along this axis. In this same preferred embodiment, axis x comprises 8 columns of drawers such that for each "day'• there are 8 opportunities for distinct medication administrations. In each of these medication administrations, one or more medications can be provided in the drawer. Using this 7 day regime, it is expected that a caregiver or other individual would be required to attend at the device once a week for 1) re-examination of the PTR for updates and changes and 2) refill of the drawers of the device. Even if this task is attended to by a paid caregiver, the economic savings of doing so once a week as compared to multiple times per day visits is enormous.

In respect of drawers 14, it is preferred that drawer liners be used to avoid contamination of various medications. Such liners can be made of plastic or paper and may be reusable or recyclable. Optionally they can be washable and reusable. Removable cup-like plastic drawer liners can be used when the medication to be taken is in liquid form. To reduce the potential of spillage when liquid medications are loaded and removed, a flip-top lid or other cover may be used with the plastic drawer liner. There are medications requiring refrigeration and in this event, it may not be preferred to place the actual medication in one of the drawers. An alert on screen 26 can simply advise the patient of the medication to be taken and the exact location (fridge, freezer etc. . . . ). For further ease of use, individual snap-lid cups containing the required unit dosage can be placed in the fridge. In the alternative, if desired, device 10 can be provided with a cooling unit such that all medications therein remain at the desired refrigeration temperature.

In a preferred form, housing 12 is an integral one piece receptacle into which the drawers fit.

In a preferred form, the signaling of messages to the patient is achieved by a means which is detectable by human senses and is based upon the pre-programmed dosing schedule mostly preferably via LCD display screen 26. It is full contemplated that there is also or alternatively audio messaging to patient via speaker 20.

In regards to the mechanism of drawer opening and closing, it is preferable that the means to enable slidable movement of drawer 14 to open and closed positions includes an arrangement of opposing pole magnets situated on both drawer 14 and the adjacent housing. The polarity of the magnets may be adjustable to hold drawer 14 in an open position until patient confirms to device that drawer has been emptied in accordance with pre-programmed dosing schedule.

For example, when drawer 14 is in a closed position relative to housing 12, magnets on each of the drawer and housing are connected by way of their respective magnetic forces (north and south poles) and as such, drawer 14 is held securely within housing 12. When the internal operating system of the device (pre-programmed with the dosing schedule) triggers an alert and/or alarm (visually via screen 26 or aurally) and lights the selected drawer 14, magnet release will occur such that the drawer can be "deployed" into an open position, thereby exposing contents. As such, magnets• must be-selected which have a sufficient magnitude of magnetism to hold closed during normal movement yet not so extraordinary a magnitude to prevent or to hinder release and opening during normal course of use. It is well within the purview of a skilled person within this art to select such magnets for this purpose and having these characteristics.

There are other means by which the drawer mechanism may operate, and the present invention should not be limited by any one such mechanism. For example, there are commonly known latch and spring (biased) mechanisms that could readily be used.

Device 10 includes an actuating means comprising a microprocessor which is programmed with a specific dosing schedule and which identifies one or more drawers which are to be opened, at any given time, in accordance with said schedule. Additionally, in a preferred form, the actuating means causes one or more drawers, which are to be opened, at any given time, in accordance with said schedule, to be illuminated. Such illumination may be via fibre optic LED lights.

Device 10 includes a programmable communication means includes a microprocessor which is programmed to manage display functions, notification functions and other operational features of the device. All microprocessors used within the device may be programmed by direct communication to a computer via USB port connection.

Device 10 may additionally include a receiver for acquiring a signal from a portable unit, to be carried by the patient, whereby the portable unit alerts the patient as to messages generated by the device. In this manner, the patient can be significantly remote from the device and still be made aware of alerts. Such a portable unit may be similar to a pager or like-sized electronic device or in the alternative could be in the form of a bracelet worn by the patient. In one embodiment, these portable units would signal to the patient via vibration. In another embodiment, these portable units would signal by visual or aural means.

The system of the present invention, comprising the device may also include a remote monitoring station with a means to contact one or more of the patient, patient's caregiver and patient's contacts when signal is received that patient is in non-compliance with drawer emptying.

The system of the present invention preferably includes a feedback means to allow the patient to confirm to device that drawer emptied in accordance with pre-programmed dosing schedule. Most preferably, this is achieved by a reset button on housing 12 which the patient is prompted to depress after emptying the drawer and after closing the emptied drawer. It is most preferred that an alarm sound and/or is visualized via screen 26 until both of these steps are taken by the patient.

In a further preferred form, the device is provided with a means by which patient compliance with medication emptying from a drawer is possible. No other device has included such a safeguard to essentially ensure consumption of the drawer contents.

Preferably, this is achieved by any means which slightly displaces the drawer, upon opening thereby preventing its closure until the liner is removed by the patient. One method of implementing this drawer displacement is by way of a small button or ball bearing at the bottom of the drawer which would lift up the liner of the drawer upon drawer opening. Once the patient actually removes the liner from the drawer, the latter would be fully close-able, as there would be no impediment by the raised liner. If the patient does not remove the liner, the drawer would not physically close and be able to be reset (hence triggering the remote monitoring and contact process). Preferably, the liner is washable and re-usable such that a caregiver/support person would visually see that the patient has taken the contents of the drawer liners. By these means, non-dosing as well as over-dosing are fully monitored and prevented.

The operation of the device of the present invention will be described with reference to all of the Figures but in particular to installation and operational flow charts of FIGS. 6-11. DMR is an acronym for Daily Medical Reminder, the system of the present invention in a preferred form.

Figure 6:
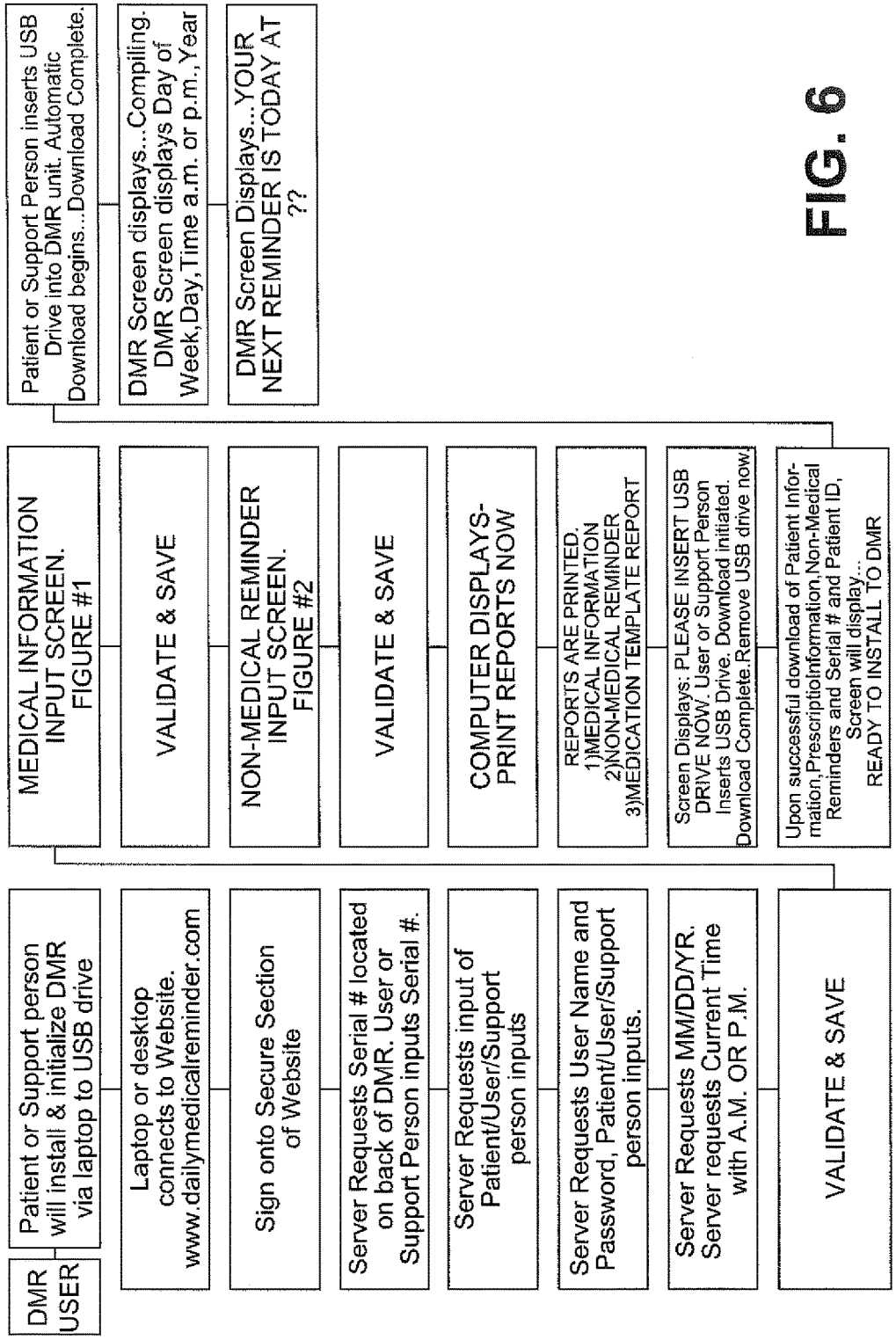
FIG. 6 is an installation flow chart.

FIG. 6 depicts a flow chart of first use and data loading by patient or his/her nominee or caregiver. The DMR is installed-initialized via a computer connected to USB device. After signing onto site of remote monitoring company personal patient details and medical details are entered, validated and saved and reports generated. The reports so generated can be transferred to DMR using USB drive. It is to be understood that such "computer" may be a desktop, a laptop or any other device having internet accessibility. In other words, a caregiver or support person could readily and effectively make the changes to the device via a smartphone such as a Blackberry® and then transfer data to the device. Compatibility can be addressed by a number of means, for example although a USB Zip drive is not compatible with the Blackberry, the care giver/support person could receive notification that the medication has been adjusted/changed/increased/decreased via his/her smart phone (email, messaging, texting) and then could proceed to sign onto the secure website via that phone and subsequently 1) download the changes to the medications and 2) physically adjust the device. The secure website would know that caregiver/support person has downloaded the new information so the next time when the USB drive is utilized, it would also update and print a new PTR (Prescription Template Report) or send as attachment to another email.

Figure 7:
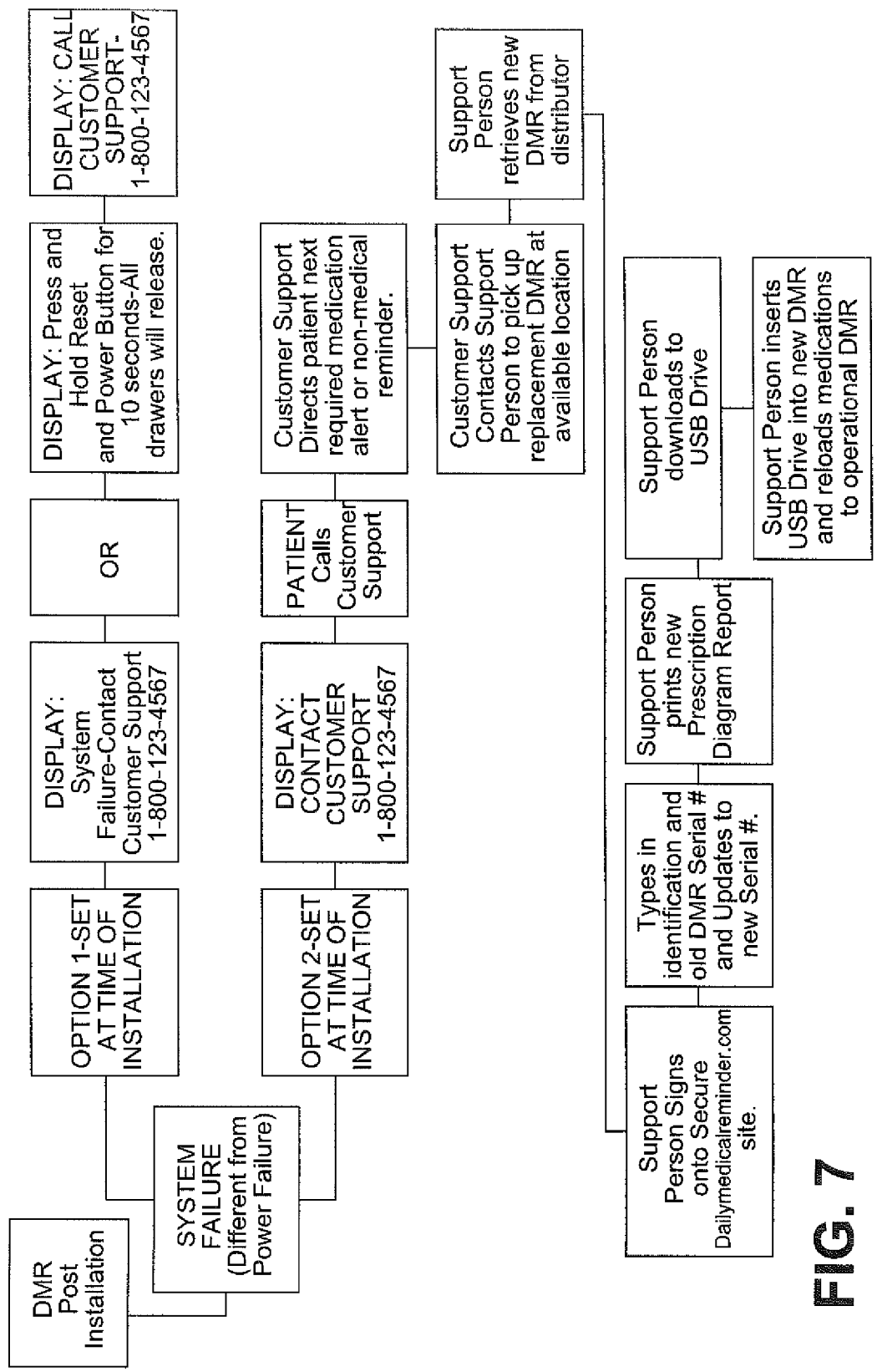
FIG. 7 is support centre operations overview.

FIG. 7 outlines installation or system failure protocols.

Figure 8:
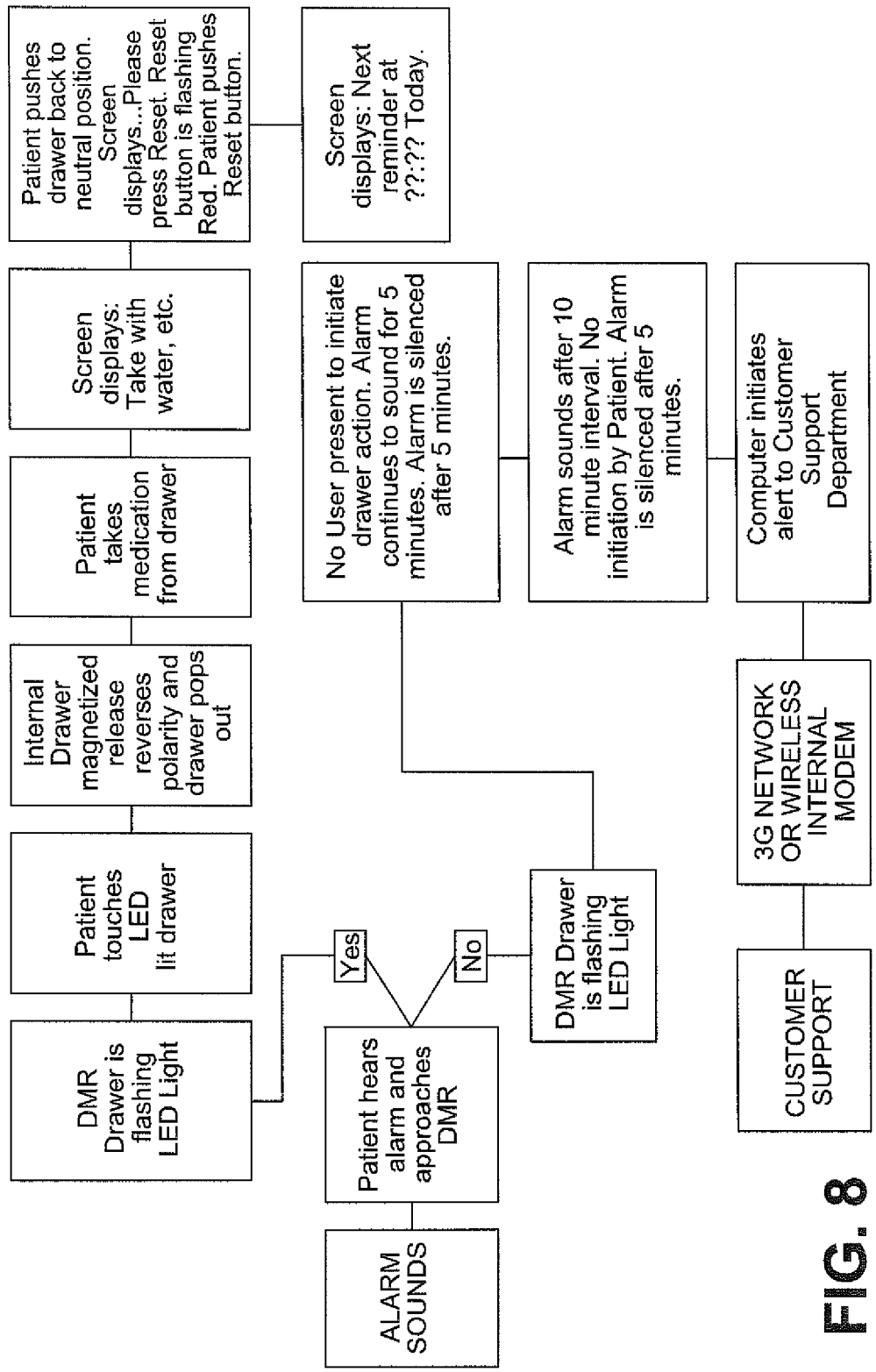
FIG. 8 is patient operations overview.

FIG. 8 outlines the protocols for patient interaction with programmed device. Upon alarm sounding, based on pre-programmed dosing schedule, there are two possible outcomes: either the patient touches LED lit drawer 14 to open it, in response to messaging or he/she does not. If patient does not, the alarm continues to sound and/be visible for a period of time (suggested as 5 minutes), is silenced and re-sounds after an interval (suggested time 10 minutes) after which point, with no response by patient, the device will initiate alert to remote monitoring system/Call Centre. This is achieved preferably via 3G, 40 or other networks or wireless internal modem.

Alternatively, if patient successfully touches drawer 14, it opens (preferably by reversing polarity of magnetized drawer-housing companion magnets) such that drawer pops open from housing 12. Patient reads messages on screen 26 or listens to verbal instructions, empties drawer and consumes medications. Patient is further alerted to close drawer and press reset button 18 which, in preferred form, will be flashing or otherwise made visible and eye-catching. With this reset, device and its feedback loop can confirm that patient has successfully followed the instructions. Screen 26 then preferably alerts patients as to next or upcoming reminders and alerts.

Figure 9:
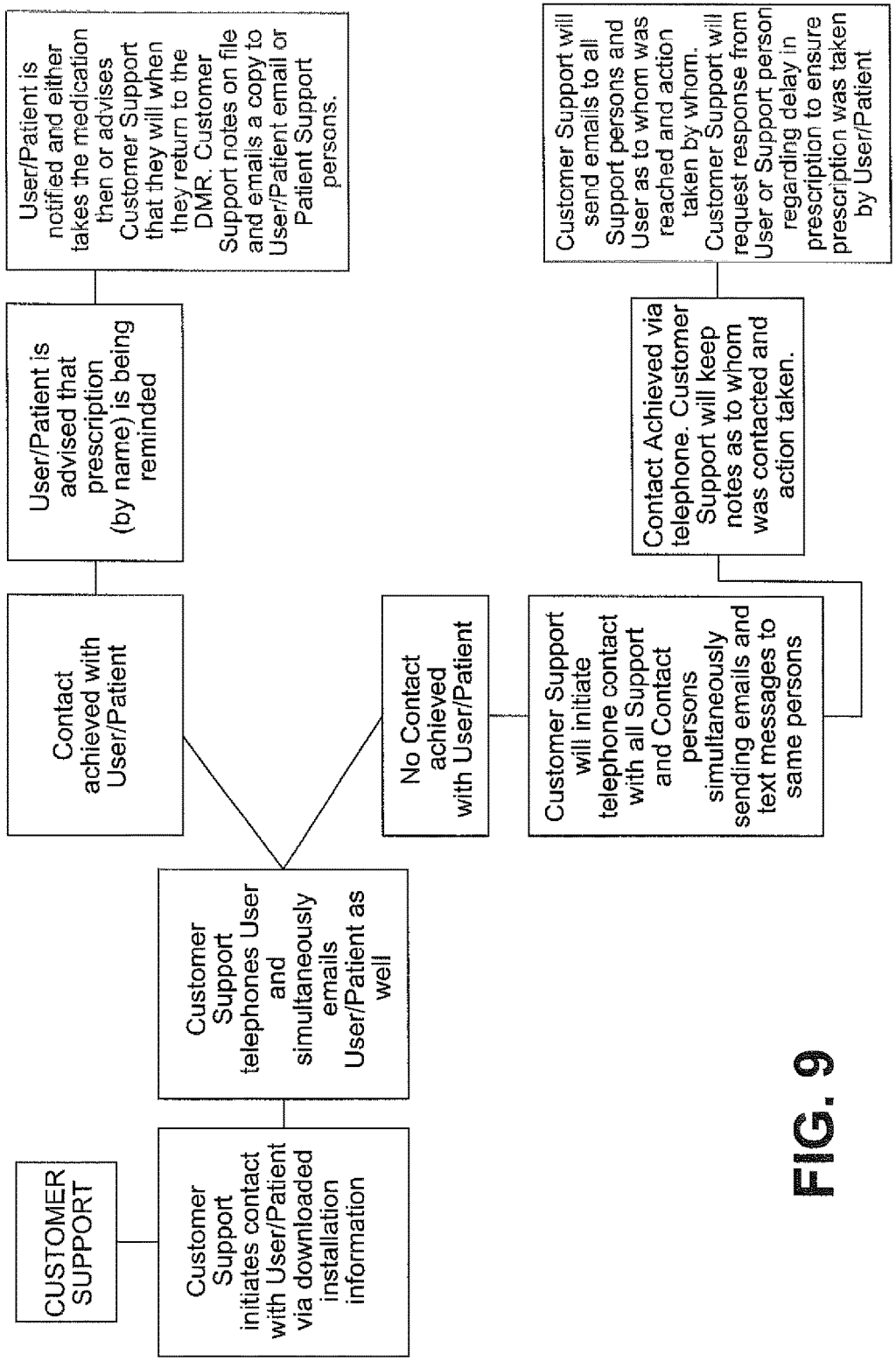
FIG. 9 is customer support operations overview.

FIG. 9 depicts the protocol for call centre response to non-compliance. There are two possible outcomes: one is remote call centre contacting user/patient successfully, reminded of missed action and monitoring action. Preferably, call centre will record action and email or text, as pre-agreed, the user/patient. The other option is non-contact with user/patient necessitating escalating actions. Such actions include calling; texting and/or emailing patient caregivers and emergency contacts. Call centre will note all communications and follow up by caregivers to correct missed action by patient.

Figure 10:
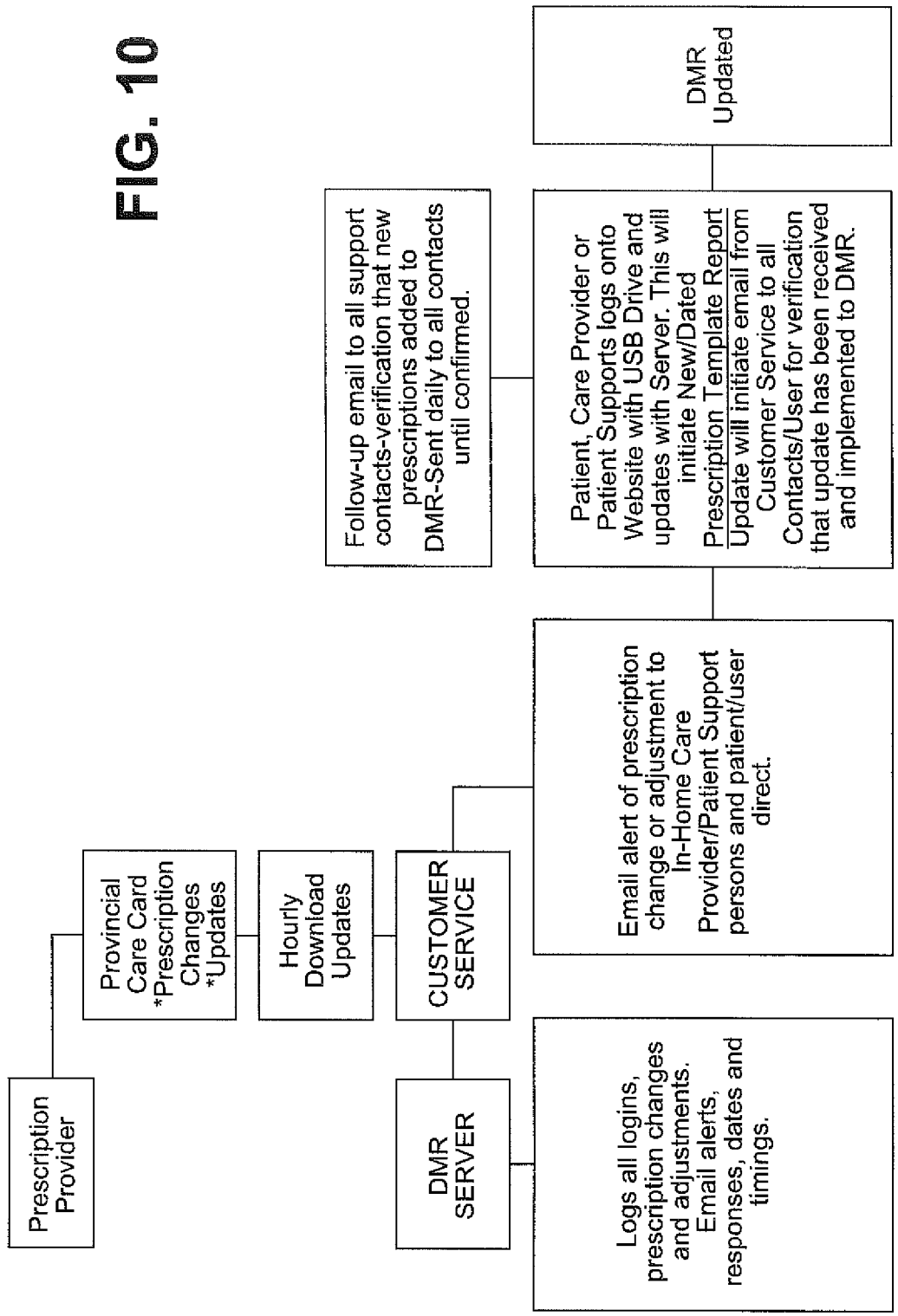
FIG. 10 prescription provider operations overview.

FIG. 10 depicts the relationship between the remote monitoring system/customer service and patient's prescription provider such that the technology of the present invention can remotely, simply and automatically update to customer service any changes to patient dosing and prescription regime. Customer service, as a hub, relays these messages to the DMR servers and also to caregivers and patient support personnel who can ensure linkage between DMR device and DMR server to transfer up-dates to device.

Figure 11:
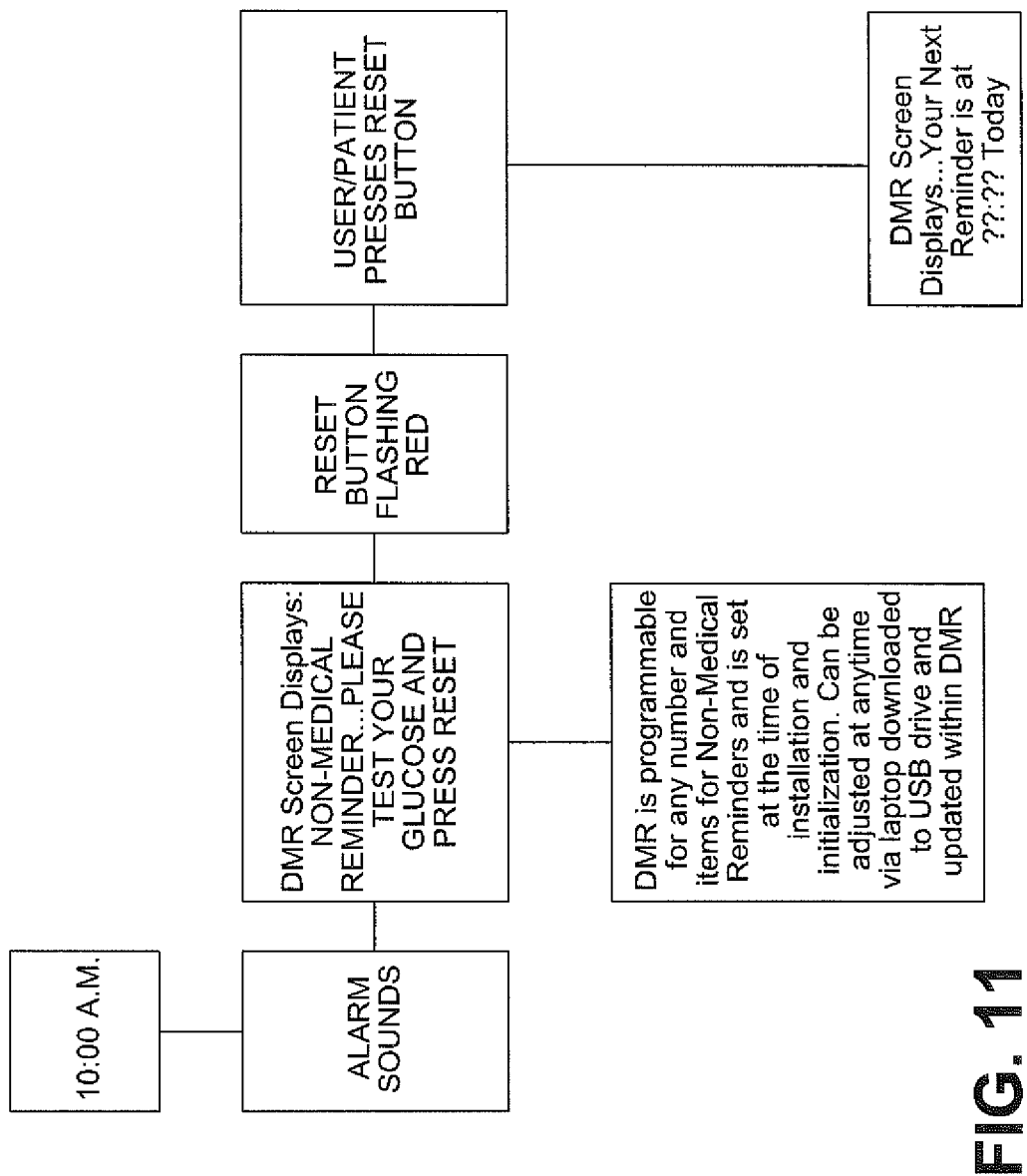
FIG. 11 is an overview of the operation of a non-medical reminder.

FIG. 11 is a protocol of the step of a non-medical reminder to a patient. These reminders may not include the requirement of any drawer opening or medication removal but will still necessitate confirmation of feedback of the particular action taken by patient, for example, the depression of reset button.

Figure 12:
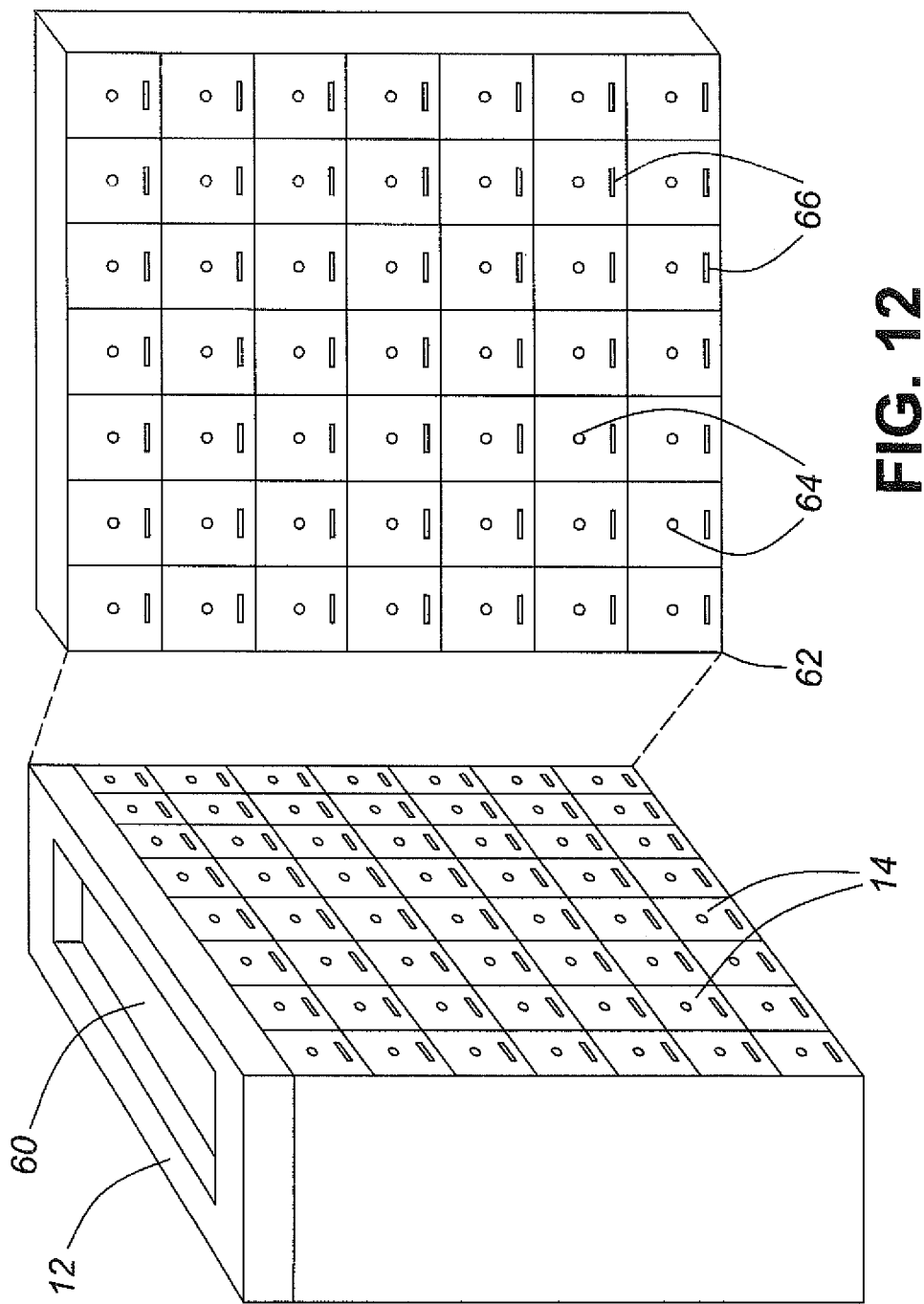
FIG. 12 a perspective view of a housing and device.

FIG. 12 provides housing 12, a plurality of drawers 14 and tablet docking station 60. A cut-away shows a front view of an LED board 62 comprising a plurality of LED lights 64 and electronic solenoid switches 66. The actual solenoid is contained within a well in the bottom of the honeycomb compartments.

Figure 13:
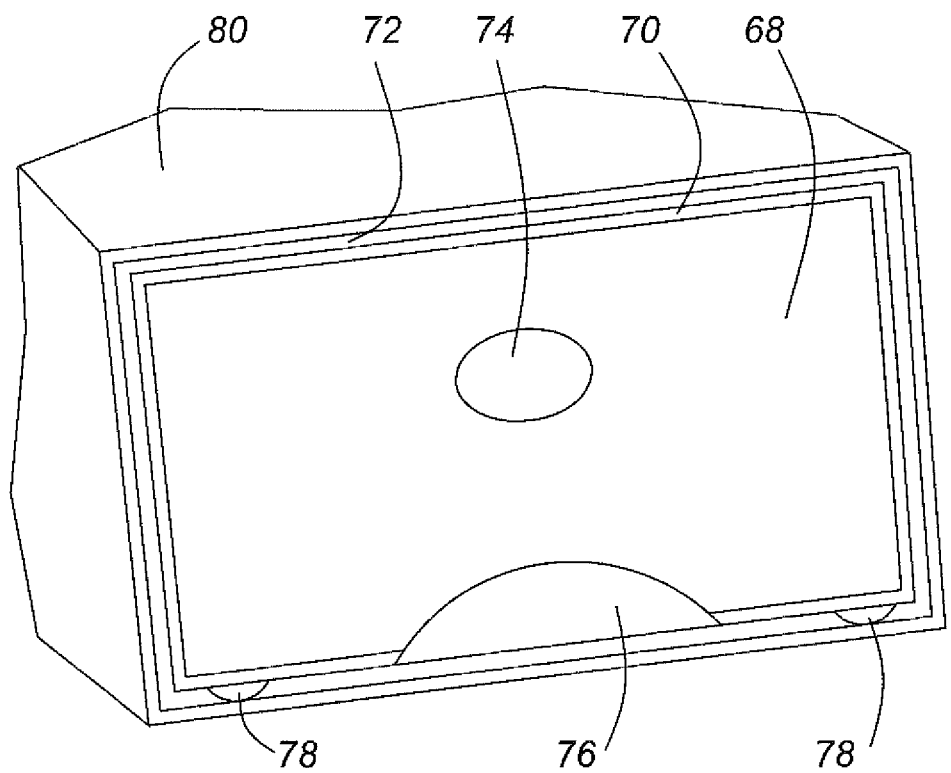
FIG. 13 is a perspective view of a drawer in situ.
Figure 14:
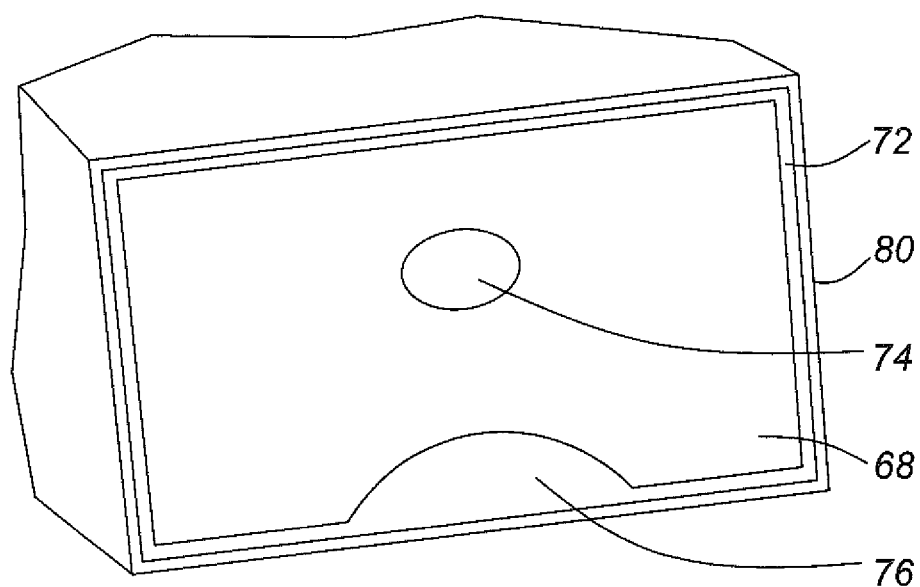
FIG. 14 is a perspective view of a drawer in situ.

FIGS. 13 and 14 show details in regards to the drawer mechanism, in a preferred form, comprising magnet board 68, drawer back 70, honeycomb 72 drawer rails 78, opening for electronic solenoid plunger 76 and hole 74 in magnet board for LED bulb. Outer casing is noted as 80.

Figure 15:
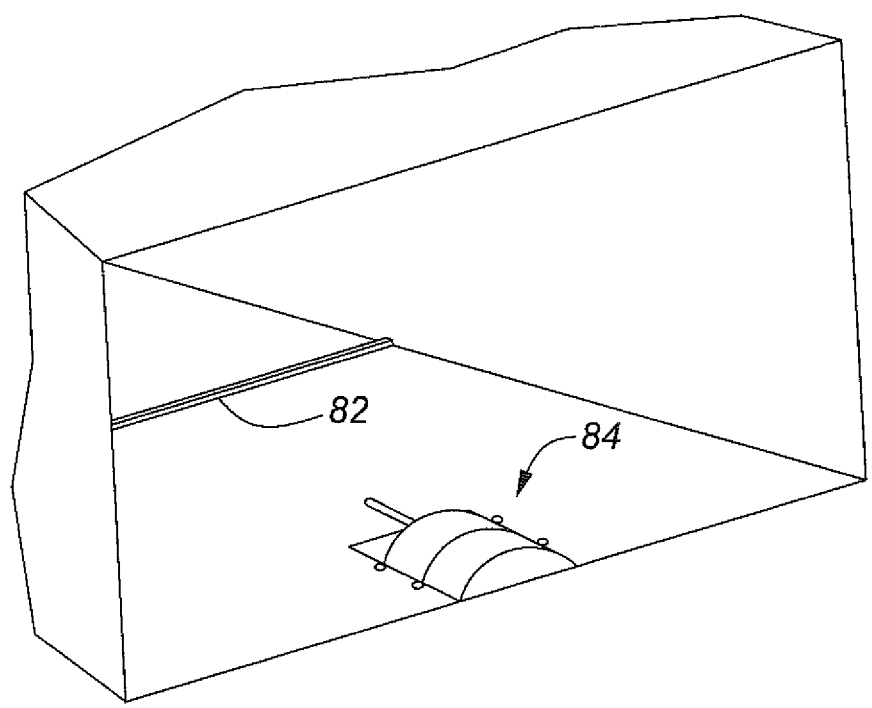
FIG. 15 is an internal view of a drawer mechanism.

FIG. 15 depicts the honeycomb section with rails 82 and electronic solenoid plunger function (shown generally at 84). The electronic solenoid plunger receives a signal from the LED board. Rail 82 will stop drawer 14 from releasing the compartment. The Plunger mechanism is securably attached to the honeycomb compartment.

Figure 16:
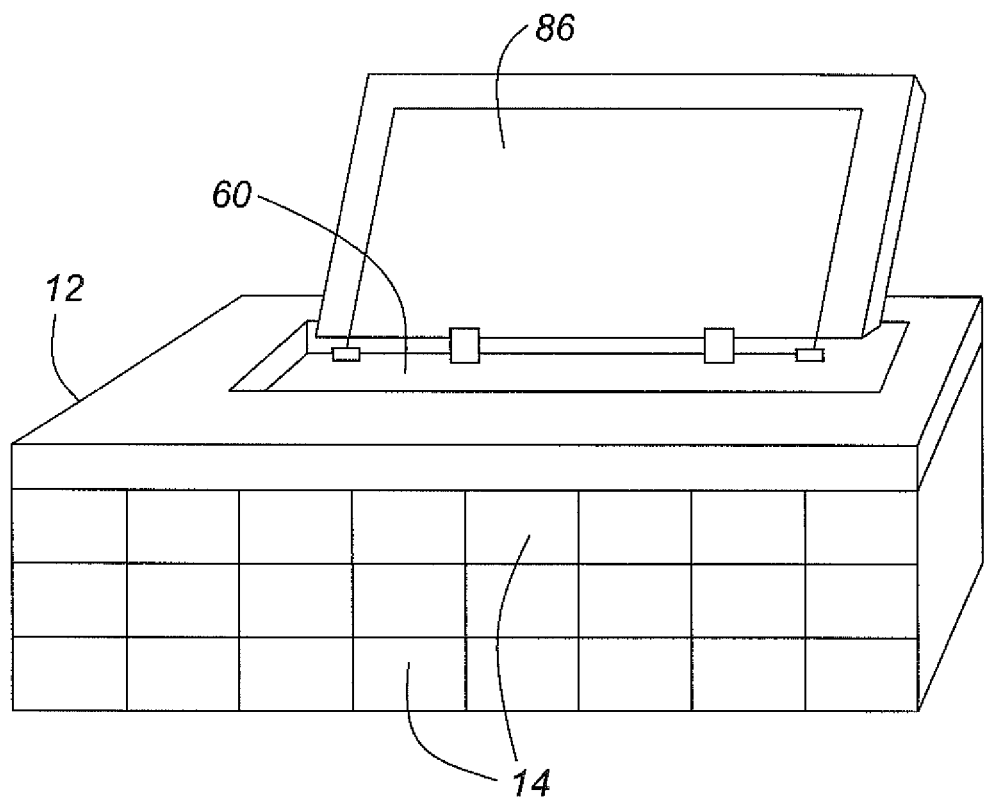
FIG. 16 a perspective view of a housing with a tablet situated on top.

FIG. 16 depicts housing 12 and docking station 60 comprising a tablet stand 86 for holding tablet in situ. Generally, the device is Ethernet capable with an internal router for at least 3G and telephone monitoring. Tablet comprises an AC-power adapter, USB port and is at least 3G capable. Tablet stand 86 securably holds tablet upright and in place.

Figure 17:
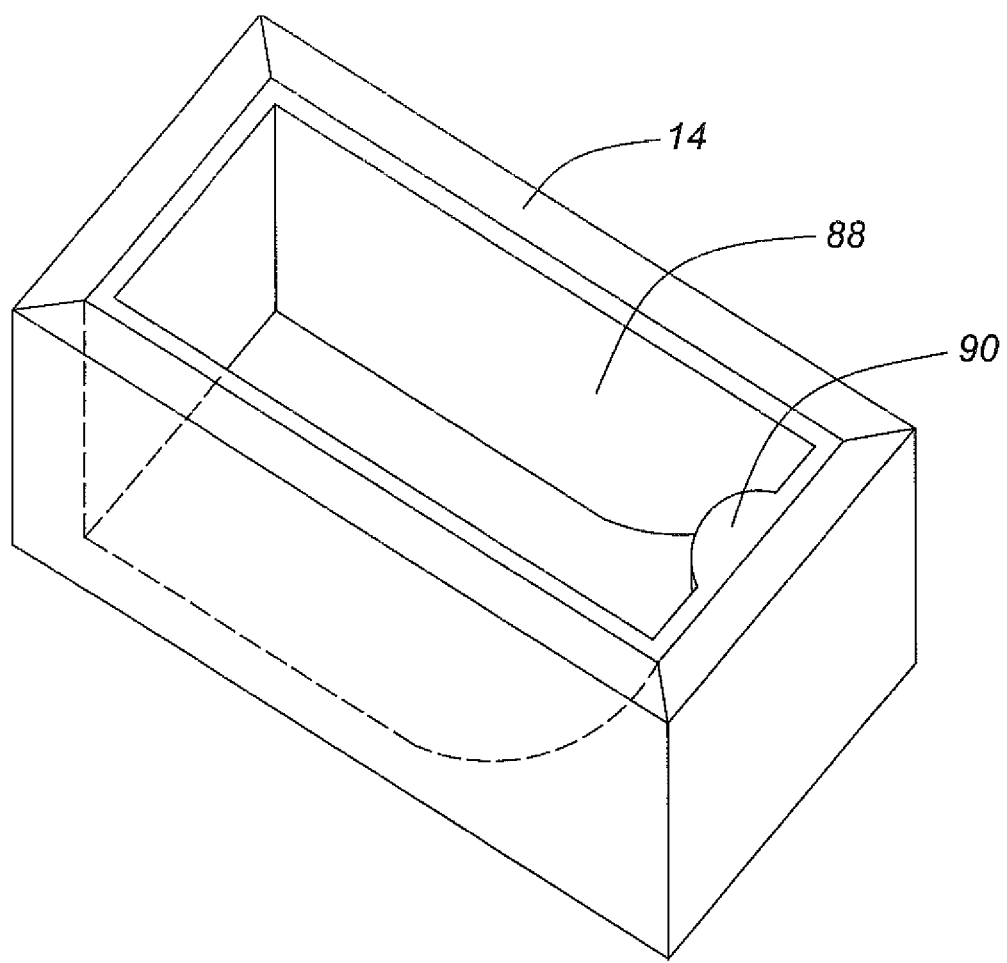
FIG. 17 is a top view of a drawer.

FIG. 17 is a top perspective view of drawer 14 in isolation including liner 88. Bottom front of the drawer is substantially solid, in a preferred form, but includes a finger pull 90 to allow ease in removal of liner 88.

In a most preferred form, the device of the present invention comprises 56 compartments/drawers (7 vertical compartments and 8 horizontal). Each drawer is preferably lined with a removable shell made of a material such as silicone and comprising finger pulls to allow user to remove the liner and take medications. The liner may be either disposable or cleanable or sterilizable such that it can be re-used. In some environments, paper liners may be preferred.

Computer Operation:

The invention can be implemented with the assistance of computing devices and in numerous ways, including as a process, an apparatus, a system, a computer readable medium such as a computer readable storage medium or a computer network wherein program instructions are sent over optical or communication links. Communication between the device and the computing devices enables the programming of the device to direct medication delivery, message conveyance and other key features of the invention. In this specification, these implementations, or any other form that the invention may take, may be referred to as computer systems or techniques. A component such as a processor or a memory described as being configured to perform a task includes both a general component that is temporarily configured to perform the task at a given time or a specific component that is manufactured to perform the task. In general, the order of the steps of disclosed processes may be altered within the scope of the invention.

The following discussion provides a brief and general description of a suitable computing environment in which various embodiments of the computer system may be implemented. Although not required, embodiments will be described in the general context of computer-executable instructions, such as program applications, modules, objects or macros being executed by a computer. Those skilled in the relevant art will appreciate that the invention can be practiced with other computer configurations, including handheld devices, multiprocessor systems, microprocessor-based or programmable consumer electronics, personal computers ("PCs"), network PCs, mini-computers, mainframe computers, and the like. The embodiments can be practiced in distributed computing environments where tasks or modules are performed by remote processing devices, which are I inked through a communications network. In a distributed computing environment, program modules may be located in both local and remote memory storage devices.

A computer system may be used as a server including one or more processing units, system memories, and system buses that couple various system components including system memory to a processing unit. Computers will at times be referred to in the singular herein, but this is not intended to limit the application to a single computing system since in some embodiments, there will be more than one computing system or other device involved. Other computer systems may be employed, such as conventional and personal computers, where the size or scale of the system allows. The processing unit may be any logic processing unit, such as one or more central processing units ("CPUs"), digital signal processors ("DSPs"), application-specific integrated circuits ("ASICs"), etc. Unless described otherwise, the construction and operation of the various components are of conventional design. As a result, such components need not be described in further detail herein, as they will be understood by those skilled in the relevant art.

A computer system includes a bus, and can employ any known bus structures or architectures, including a memory bus with memory controller, a peripheral bus, and a local bus. The computer system memory may include read-only memory ("ROM") and random access memory ("RAM"). A basic input/output system ("BIOS"), which can form part of the ROM, contains basic routines that help transfer information between elements within the computing system, such as during startup.

The computer system also includes non-volatile memory. The non-volatile memory may take a variety of forms, for example a hard disk drive for reading from and writing to a hard disk, and an optical disk drive and a magnetic disk drive for reading from and writing to removable optical disks and magnetic disks, respectively. The optical disk can be a CD-ROM, while the magnetic disk can be a magnetic floppy disk or diskette. The hard disk drive, optical disk drive and magnetic disk drive communicate with the processing unit via the system bus. The hard disk drive; optical disk drive and magnetic disk drive may include appropriate interfaces or controllers coupled between such drives and the system bus, as is known by those skilled in the relevant art. The drives, and their associated computer-readable media, provide non-volatile storage of computer readable instructions, data structures, program modules and other data for the computing system. Although a computing system may employ hard disks, optical disks and/or magnetic disks, those skilled in the relevant art will appreciate that other types of non-volatile computer-readable media that can store data accessible by a computer system may be employed, such a magnetic cassettes, flash memory cards, digital video disks ("DVD"), Bernoulli cartridges, RAMs, ROMs, smart cards, etc.

Various program modules or application programs and/or data can be stored in the computer memory. For example, the system memory may store an operating system, end user application interfaces, server applications, and one or more application program interfaces ("APIs").

The computer system memory also includes one or more networking applications, for example a Web server application and/or Web client or browser application for permitting the computer to exchange data with sources via the Internet, corporate intranets, or other networks as described below, as well as with other server applications on server computers such as those further discussed below. The networking application in the preferred embodiment is markup language based, such as hypertext mark p language ("HTML"), extensible markup language ("XML") or wireless markup language ("WML"), and operates with markup languages that use syntactically delimited characters added to the data of a document to represent the structure of the document. A number of Web server applications and Web client or browser applications are commercially available, such those available from Mozilla and Microsoft and the like.

The operating system and various applications/modules and/or data can be stored on the hard disk of the hard disk drive, the optical disk of the optical disk drive and/or the magnetic disk of the magnetic disk drive.

A computer system can operate in a networked environment using logical connections to one or more client computers and/or one or more database systems, such as one or more remote computers or networks. A computer may be logically connected to one or more client computers and/or database systems under any known method of permitting computers to communicate, for example through a network such as a local area network ("LAN") and/or a wide area network ("WAN") including, for example, the Internet. Such networking environments are well known including wired and wireless enterprise-wide computer networks, intranets, extranets, and the Internet. Other embodiments include other types of communication networks such as telecommunications networks, cellular networks, paging networks, and other mobile networks. The information sent or received via the communications channel may, or may not be encrypted. When used in a LAN networking environment, a computer is connected to the LAN through an adapter or network interface card (communicatively linked to the system bus). When used in a WAN networking environment, a computer may include an interface and modem or other device, such as a network interface card, for establishing communications over the WAN/Internet.

In a networked environment, program modules, application programs, or data, or portions thereof, can be stored in a computer for provision to the networked computers. In one embodiment, the computer is communicatively linked through a network with TCP/IP middle layer network protocols; however, other similar network protocol layers are used in other embodiments, such as user datagram protocol ("UDP"). Those skilled in the relevant art will readily recognize that these network connections are only some examples of establishing communications links between computers, and other links may be used, including wireless links.

While in most instances a computer will operate automatically, where an end user application interface is provided, a user can enter commands and information into the computer through a user application interface including input devices, such as a keyboard, and a pointing device, such as a mouse. Other input devices can include a microphone, joystick, scanner, etc. These and other input devices are connected to the processing unit through the user application interface, such as a serial port interface that couples to the system bus, although other interfaces, such as a parallel port, a game port, or a wireless interface, or a universal serial bus ("USB") can be used. A monitor or other display device is coupled to the bus via a video interface, such as a video adapter (not shown). The computer can include other output devices, such as speakers, printers, etc.

It is most preferred that the outer casing of the housing comprises a docking station into which a tablet (Operation Tablet) can be inserted for operable connection. The Operation Tablet (which can be any known tablet such as iPAD®, Blackberry Playbook® and the like) is preprogrammed and comprises a USB port which is connected to the DMR device. It would most likely run on 110 v AC power. The Operation Tablet generally has a backup battery pack of four hours and an additional option for a further 24 hours of backup power.

In preferred operation, the bottom of each drawer will slide on rails and a section of the bottom of each drawer will house the electronic solenoid piston to push out the drawer upon signal from the user. At the pre-programmed medication alert time, an auditory signal will sound, the user will approach the device and advise via a touch screen that he or she is accepting the notification. The drawer will be lit by the internal LED light. The piston will expel against the drawer and the drawer will move forward approximately 1" at which time the patient/user will assist the drawer opening and remove the silicone liner. The user will then push the drawer back to its neutral position, the magnetized back of the drawer will connect with the LED board and be re-magnetized into the closed and locked position.

It is preferred that behind the honeycomb arrangement of drawers that there is a magnetized board with LED light and small switch that is installed to signal the piston. It is preferred that behind the LED board is the compartment that will house the backup power system, router and Ethernet connection. It is preferred that the back casing will latch on three sides of the DMR casing.

While the forms of the device, drawers, housing, method and system described herein constitute preferred embodiments of this invention, it is to be understood that the invention is not limited to these precise forms. As will be apparent to those skilled in the art, the various embodiments described above can be combined to provide further embodiments. Aspects of the present systems, methods and nodes (including specific components thereof) can be modified, if necessary, to best employ the systems, methods, nodes and components and concepts of the invention. These aspects are considered fully within the scope of the invention as claimed. For example, the various methods described above may omit some acts, include other acts, and/or execute acts in a different order than set out in the illustrated embodiments.

Further, in the methods taught herein, the various acts may be performed m •a different order than that illustrated and described. Additionally, the methods can omit some acts, and/or employ additional acts.

These and other changes can be made to the present systems, methods and articles in light of the above description. In general, in the following claims, the terms used should not be construed to limit the invention to the specific embodiments disclosed in the specification and the claims, but should be construed to include all possible embodiments along with the full scope of equivalents to which such claims are entitled. Accordingly, the invention is not limited by the disclosure, but instead its scope is to be determined entirely by the following claims.

The invention claimed is:

1. A medication reminder and dispensing device for dispensing at least one dose of a medication to a patient in accordance with a pre-programmed schedule, the device comprising:
   a housing comprising at least one opening extending inwardly from a surface thereof;
   at least one medication holding drawer containing the at least one dose, the drawer being slidably positioned in the at least one opening and configured to move from a closed position to an open position to expose an interior of the drawer;
   at least one electromagnet connected to the housing or drawer configured to be transitioned between a first state and a second state, wherein, when in the first state, the electromagnet is configured to maintain the drawer in the closed position, and, when in the second state, the drawer automatically moves to the open position;
   a patient input component configured to receive a confirmation from the patient that the drawer has been emptied of the at least one dose; and
   a processor configured to:
      cause the at least one electromagnet to transition from the first state to the second state based on the pre-programmed schedule, thereby causing the drawer to automatically move to the open position;
      receive a confirmation from the patient by the patient input component that the drawer has been emptied of the at least one dose contained therein, and
      generate an alert that the patient is not in compliance with the pre-programmed schedule when the confirmation is not received within a predetermined period of time from opening of the drawer.

2. The device of claim 1, further comprising a visual or audio feedback component, wherein the processor is configured to cause the visual or audio feedback component to provide a message prompting the patient to take the at least one dose of the medication according to the pre-programmed schedule.

3. The device of claim 2, wherein the visual or audio feedback component comprises a touch-enabled LCD display screen.

4. The device of claim 1, further comprising a communication interface operatively coupled to the processor capable of receiving signals at and communicating signals from the medication reminder and dispensing device, wherein the processor is configured to cause the communication interface to transmit the alert to a remote monitoring station.

5. The system of claim 4, wherein the communications interface is configured to connect to the remote monitoring station via one or more of a wired connection, a LAN connection, a 3G Wi-Fi connection, and a 4G Wi-Fi connection.

6. The device of claim 1, further comprising one or more rails mounted between the housing and the medication holding drawer configured to allow the drawer to move from the closed position to the open position.

7. The device of claim 1, further comprising an indicator mounted on the drawer or on the surface of the housing adjacent to the drawer, wherein the processor is configured to activate the indicator when the drawer is being opened based on the pre-programmed schedule.

8. The system of claim 7, wherein the indicator comprises one or more LED bulbs positioned to illuminate at least the interior of the drawer.

9. The device of claim 1, wherein the housing comprises a plurality of openings and a plurality of medication holding drawers, and wherein a drawer is positioned in each of the plurality of openings.

10. The device of claim 9, wherein the plurality of openings are arranged in a grid on the surface of the housing, the grid comprising seven columns of openings.

11. The device of claim 10, wherein the grid further comprises eight rows of openings.

12. The device of claim 1, wherein the patient input component comprises a computer or tablet, and wherein the medication reminder and dispensing device further comprises a docking station which connects the computer or tablet to the housing and places the computer or tablet in electronic communication with the processor.

13. The device of claim 1, wherein the at least one drawer comprise a removable liner partially enclosing the interior of the drawer configured to contain the at least one dose, and wherein, as the drawer moves to the open position, the removable liner is configured to move to a lifted-up position.

14. The device of claim 13, wherein, when the removable liner is in the lifted-up position, the removable liner is configured to block the drawer from moving to the closed position such that the drawer does not close until the removable liner is removed from the interior of the drawer.

15. The device of claim 1, further comprising a spring mounted adjacent to the at least one drawer biased to contribute to moving the at least one drawer to the open position when the electromagnet is in the second state.

16. The device of claim 1, wherein the drawer comprises a pole magnet capable of reversing polarity configured to be repelled by the electromagnet when the electromagnet is in the second state, to open the drawer.

17. The device of claim 16, wherein, upon receiving the confirmation of the patient input component, the processor is configured to cause the pole magnet of the at least one drawer to reverse polarity, thereby causing the drawer to automatically move to the closed position.

18. A system for dispensing medication to a patient in accordance with a pre-programmed schedule, comprising:
a medication reminder and dispensing device for dispensing at least one dose of the medication to the patient, the device comprising:
a housing comprising at least one opening extending inwardly from a surface thereof;
at least one medication holding drawer containing the at least one dose, the drawer being slidably positioned in the at least one opening and configured to move from a closed position to an open position to expose an interior of the drawer;
at least one electromagnet connected to the housing or drawer configured to be transitioned between a first state and a second state, wherein, when in the first state, the electromagnet is configured to maintain the drawer in the closed position, and, when in the second state, the drawer automatically moves to the open position;
a patient input component configured to receive a confirmation from the patient that the drawer has been emptied of the at least one dose; and
a processor configured to:
cause the at least one electromagnet to transition from the first state to the second state based on the pre-programmed schedule, thereby causing the drawer to automatically move to the open position;
receive a confirmation from the patient by the patient input component that the drawer has been emptied of the at least one dose contained therein, and
generate an alert that the patient is not in compliance with the pre-programmed schedule when the confirmation is not received within a predetermined period of time from opening of the drawer; and
a wearable messaging device configured to be worn by the patient in wireless communication with the processor of the medication reminder and dispensing device, wherein the processor is configured to cause the wearable messaging device to display a message to the patient prompting the patient to take the at least one dose of the medication in the drawer based on the pre-programmed schedule.

19. The system of claim 18, wherein the wearable messaging device comprises a bracelet.

20. The system of claim 18, further comprising a remote monitoring station in electrical communication with the medication reminder and dispensing device, wherein the processor of the medication reminder and dispensing device is configured to transmit the alert that the patient is not in compliance with the pre-programmed schedule from the medication reminder and dispensing device to the remote monitoring station.

* * * * *